United States Patent
Dionne et al.

(10) Patent No.: US 9,011,699 B2
(45) Date of Patent: Apr. 21, 2015

(54) ULTRASONIC AGGLOMERATION OF MICROALGAE

(75) Inventors: Jason Dionne, Simsbury, CT (US); Jeff King, Coventry, CT (US); Bart Lipkens, Hampden, MA (US); Edward A. Rietman, Nashua, NH (US)

(73) Assignee: FloDesign Sonics, Inc., Wilbraham, MA (US)

( * ) Notice: Subject to any disclaimer, the term of this patent is extended or adjusted under 35 U.S.C. 154(b) by 770 days.

(21) Appl. No.: 13/216,035

(22) Filed: Aug. 23, 2011

(65) Prior Publication Data

US 2012/0328477 A1 Dec. 27, 2012

Related U.S. Application Data

(60) Provisional application No. 61/402,080, filed on Aug. 23, 2010.

(51) Int. Cl.
| | | |
|---|---|---|
| C02F 1/36 | (2006.01) | |
| C02F 1/52 | (2006.01) | |
| B06B 1/00 | (2006.01) | |
| B06B 1/06 | (2006.01) | |
| C12M 1/26 | (2006.01) | |
| C12M 1/00 | (2006.01) | |

(52) U.S. Cl.
CPC .............. *B06B 1/0625* (2013.01); *C12M 33/12* (2013.01); *C12M 33/22* (2013.01); *C12M 47/02* (2013.01)

(58) Field of Classification Search
CPC .......... C02F 1/52; B01D 21/283; B01D 43/00
USPC ................ 210/738, 748.05; 422/128
See application file for complete search history.

(56) References Cited

U.S. PATENT DOCUMENTS

| | | | | |
|---|---|---|---|---|
| 4,055,491 | A * | 10/1977 | Porath-Furedi | 210/738 |
| 4,165,273 | A | 8/1979 | Azarov et al. | |
| 5,225,089 | A | 7/1993 | Benes et al. | |
| 5,711,888 | A * | 1/1998 | Trampler et al. | 210/748.05 |
| 5,951,456 | A * | 9/1999 | Scott | 516/195 |
| 6,482,327 | B1 * | 11/2002 | Mori et al. | 210/695 |
| 6,487,095 | B1 | 11/2002 | Malik et al. | |
| 6,749,666 | B2 * | 6/2004 | Meegan, Jr. | 95/29 |
| 2002/0134734 | A1 | 9/2002 | Campbell et al. | |
| 2003/0195496 | A1 | 10/2003 | Maguire et al. | |
| 2003/0230535 | A1 | 12/2003 | Affeld et al. | |

(Continued)

FOREIGN PATENT DOCUMENTS

WO WO-2009111276 A1 9/2009

OTHER PUBLICATIONS

B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009.

(Continued)

*Primary Examiner* — Kevin Joyner
(74) *Attorney, Agent, or Firm* — Richard M. Klein; Fay Sharpe LLP (57) ABSTRACT

Systems are provided with varying flow chamber configurations which acoustically agglomerate microorganisms such as algae for separation from a host fluid such as water. Related apparatus, systems, techniques and articles are also described.

14 Claims, 11 Drawing Sheets

(56) References Cited

U.S. PATENT DOCUMENTS

| | | |
|---|---|---|
| 2007/0272618 A1 | 11/2007 | Gou et al. |
| 2010/0000945 A1 | 1/2010 | Gavalas |
| 2011/0092726 A1 | 4/2011 | Clarke |
| 2011/0123392 A1 | 5/2011 | Dionne et al. |

OTHER PUBLICATIONS

B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A) 2008.

B. Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008.

B. Lipkens, M. Costolo, and E. Rietman, "The effect of frequency sweeping and fluid flow on particle trajectories in ultrasonic standing waves", IEEE Sensors Journal, vol. 8, No. 6, pp. 667-677, 2008.

Castro, V. E., "Tunable gap and quantum quench dynamics in bilayer graphene"; Jul. 13, 2010, Mathematica Summer School.

Garcia-Lopez, "Enhanced Acoustic Separation of Oil-Water Emulsion in Resonant Cavities", The Open Acoustics Journal, pp. 66-71, 2008.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

L. P. Gor'kov, "On the forces acting on a small particle in an acoustical field in an ideal fluid," Soy. Phys. Dokl., vol. 6, pp. 773-775, 1962.

Meribout, et al., "An Industrial-Prototype Acoustic Array for Real-Time Emulsion Layer Detection in Oil Storage Tanks", IEEE Sensors Journal, vol. 9, No. 12, Dec. 2009.

Pangu, et al., "Droplet transport and coalescne kinetecs in emulsions subjected to acoustic fields", Ultrasonics 46, pp. 289-302 (2007).

Ponomarenko et al. "Density of states and zero Landau level probed through capacitance of graphene"; Nature Nanotechnology Letters; Jul. 5, 2009; DOI: 10.1038/NNANO.2009.177.

Sony News Release: <http://www.sony.net/SonyInfo/News/Press/201010/10-137E/index.html>, Oct. 2010.

\* cited by examiner

ULTRASONIC AGGLOMERATION OF MICROALGAE

RELATED APPLICATION

This application claims priority to U.S. Pat. App. Ser. No. 61/402,080 filed on Aug. 23, 2010, the contents of which are hereby fully incorporated by reference.

TECHNICAL FIELD

The subject matter described herein relates to techniques for ultrasonically agglomerating microalgae for applications such as biofuel and nutraceutical production.

BACKGROUND

Currently, there is great interest in the use of alternative renewable biofuels, such as biodiesel, that can be produced from biooil feedstocks that are in turn produced by oleaginous microorganisms such as microalgae, bacillus, fungi, and yeast. Oleaginous microorganisms are microbial with lipid content typically in excess of 20%. A renewable liquid fuel energy source could play a significant role in reducing our national dependence on foreign oil imports. Reported in the literature is that oleaginous yeasts and microalgae can grow and accumulate significant amounts of lipids (see A. Banerjee, R. Sharma, Y. Chisti and U. C. Banerjee, "*Botryococcus Braunii*: A renewable source of hydrocarbons and other chemicals" Critical Reviews in Biotechnology, 22 (3), 245-279, 2002; Y. Chisti, "Biodiesel from microalgae beats bioethanol" Trends in Biotechnology, 26 (3), 126-131, 2007; P. Metzger and C. Largeau, "*Botryococcus braunii*: a rich source for hydrocarbons and related ether lipids" Appl. Microbiol. Biotechnol, 66, 486-496, 2005; X. Meng, J. Yang, X. Xu, L. Zhang, Q. Nie, M. Xian "Biodiesel production from oleaginous microorganisms" Renewable Energy, 34, 1-5, 2009, the contents of each of the aforementioned papers being incorporated by reference). The oil content and composition are a function of the type of microorganisms used and the conditions in which the culturing took place. As an example, microalgae are sunlight driven cell factories that convert carbon dioxide to potential biofuels. Microalgae grow at a very fast pace, doubling their biomass within a 24 hour time period and are rich in oil. The lipid content of microalgae can be as high as 70%. In particular, microalgae are reported to be excellent candidates for biodiesel production because of their higher biomass production, higher photosynthetic efficiency, and faster growth compared to most other energy crops.

Most of the work reported in the literature on the development of microbial oil production has focused on the identification of better strains of oleaginous microorganisms, on genetic and metabolic engineering of strains, on the development of the optimal environmental conditions for microorganism growth, and on the development of the optimal energy sources to fuel the growth of the microorganisms.

Similar to the biofuel studies there have been studies on chemical and nutraceutical production in microalgae (see J. N. Rosenberg, G. A. Oyler, L. Wilkinson and M. J. Betenbaugh, "A green light for engineered algae: redirection metabolism to fuel a biotechnology revolution", Current Opinion in Biotechnology, 19, 430-436, 2008, the contents of which are hereby incorporated by reference). However there has been little effort spent on the harvesting of microorganisms, particularly from large-scale (100 liter to 2 million liter) volume cultures. Therefore, significant challenges remain in the energy efficient and economical harvesting of microorganisms from their host medium, as well as steps to collect the microbial oils. In particular, harvesting of the microorganisms by the concentration and separation of the microorganisms from their host medium, typically water.

Algae use in bioreactors or large ponds is increasingly being employed for biofuels and nutraceuticals. Metzger, and Largeau (2005) and Banerjee (2002) describe the use of *Botryococcus braunii* as a source of hydrocarbons and similar lipids, such as $C_{27}$diane, $C_{30}$ botryococcene, squalene, tetramethylsqualene and trs,trs-lycopadine, among others including ether lipids, epoxides and sterols. Weldy and Huesemann (C. S. Weldy and M. Huesemann, "Lipid production by *Dunaliella salina* in batch culture: effects of nitrogen limitation and light intensity" U.S. Department of Energy Journal of Undergraduate Research, Vol. VII, 115-122, 2007) and Hejazi and Wijffels (M. A. Hejazi and R. H. Wijffels, "Effect of light intensity on beta-carotene production and extraction by *Dunaliella salina* in two-phase bioreactors" Biomolecular Engineering, 20, 171-175, 2003) describe the use of *Dunaliella salina*, for lipid production and beta-carotene production. Other researchers, including Chisti (2007), Meng et al. (2009) and Hu (Q. Hu, M. Sommerfeld, E. Jarvis, M. Ghirardi, M. Posewitz, M. Seibert, and A. Darzins, "Microalgae triacylglycerols as feedstocks for biofuel production: perspectives and advances" The Plant Journal, 54, 621-639, 2008) discuss the use of microalgae for biodeisel and triacylglycerols production. Lastly, Rosenberg et al (2008) describe a whole list of nutraceutical, pharmaceuticals, and high-value chemicals produced from microalgae. In all these applications, there is a need for improved algae concentrating, or as is known, dewatering. Conventional techniques involve batch centrifuging at high-cost and high energy.

SUMMARY

In one aspect, a system includes a primary flow channel through which is flowed a mixture of a host fluid and algae with the primary flow channel having an inlet and extending to a terminus, a first outlet channel extending from the primary flow channel at a point between the inlet and the terminus to a settling tank, a second outlet channel extending from the primary flow channel at the terminus to the settling tank, a first array of transducers disposed within the primary flow channel between the inlet and the first outlet channel for acoustically agglomerating the algae, and a second array of transducers disposed within the primary flow channel between the first outlet channel and the terminus for further acoustically agglomerating the algae.

The system in some implementations can include a third array of transducers disposed within the first outlet channel for further acoustically agglomerating the algae, and/or a fourth array of transducers disposed within the second outlet channel for further acoustically agglomerating the algae.

At least one first ring transducer can be disposed within the primary flow channel between the first array of transducers and the second array of transducers for further acoustically agglomerating the algae. Similarly, at least one second ring transducer can be disposed within the first outlet channel between the primary flow channel and the third array of transducers for further acoustically agglomerating the algae. Furthermore, at least one third ring transducer can be disposed within the second outlet channel between the primary flow channel and the fourth array of transducers for further acoustically agglomerating the algae. At least a portion of the transducers within the channels can be flat transducers.

The host fluid and algae can be gravitationally fed into at least one of the primary fluid channel, the first outlet channel and the second outlet channel. Alternatively, the system can include a pump for introducing the host fluid and algae into the primary fluid channel. The host fluid can be water. The system can include a reservoir containing the host fluid and algae prior to introduction in to the primary fluid channel. The system can also include the settling tank which in turn can comprise at least one water outlet through which water can be removed after the algae has settled and at least one algae outlet to facilitate removal of the algae.

In an interrelated aspect, a system comprises a flow chamber through which is flowed a mixture of a host fluid and algae. The flow chamber includes at least one inlet through which the host fluid and algae enters the flow chamber, at least one water outlet through which water exits the flow chamber; and an algae outlet through which agglomerated algae exits the flow chamber into a settling tank. A first array of transducers can be disposed between the at least one inlet and the at least one water outlet for acoustically agglomerating the algae.

In some variations, a second array of transducers can be disposed between the at least one inlet and the algae outlet for further acoustically agglomerating the algae. A pump can introduce the host fluid and algae into the flow chamber and/or the host fluid and algae are gravitationally fed into the flow chamber. The host fluid can be water. A reservoir can be provided that contains the host fluid and algae prior to introduction in to the flow chamber. The system can also include the settling tank which comprises at least one water outlet through which water can be removed after the algae has settled and at least one algae outlet to facilitate removal of the algae.

The transducers with this arrangement can be tubular transducers which are optionally positioned in parallel in a vertical orientation (relative to gravity).

The current subject matter provides many advantages. For example, the current subject matter enables the processing of large quantities of a host medium (e.g., water, etc.) that is laden with oleaginous microorganisms by efficiently trapping, concentrating, and separating the microorganisms.

The details of one or more variations of the subject matter described herein are set forth in the accompanying drawings and the description below. Other features and advantages of the subject matter described herein will be apparent from the description and drawings, and from the claims.

DETAILED DESCRIPTION

This current subject matter is directed to large-scale acoustophoretic technology to collect and process microalgae for the production of nutraceuticals and biofuels. As is described below, an ultrasonic standing wave will induce agglomeration of microalgae. These agglomerates will become larger and larger, finally overcoming fluid flow and acoustic force and drop out of the fluid stream due to gravity. They are collected in a large settling tank where the, now algae mats, can be processed for nutraceutical and biofuel extraction. It is noted that the acoustic pressure at the standing wave nodes tends to rupture many of the algae cells and force the nutraceuticals and biofuels out into the water stream where they may be separated by further acoustophoresis techniques or other methods (e.g. chromatography).

Figure 1:
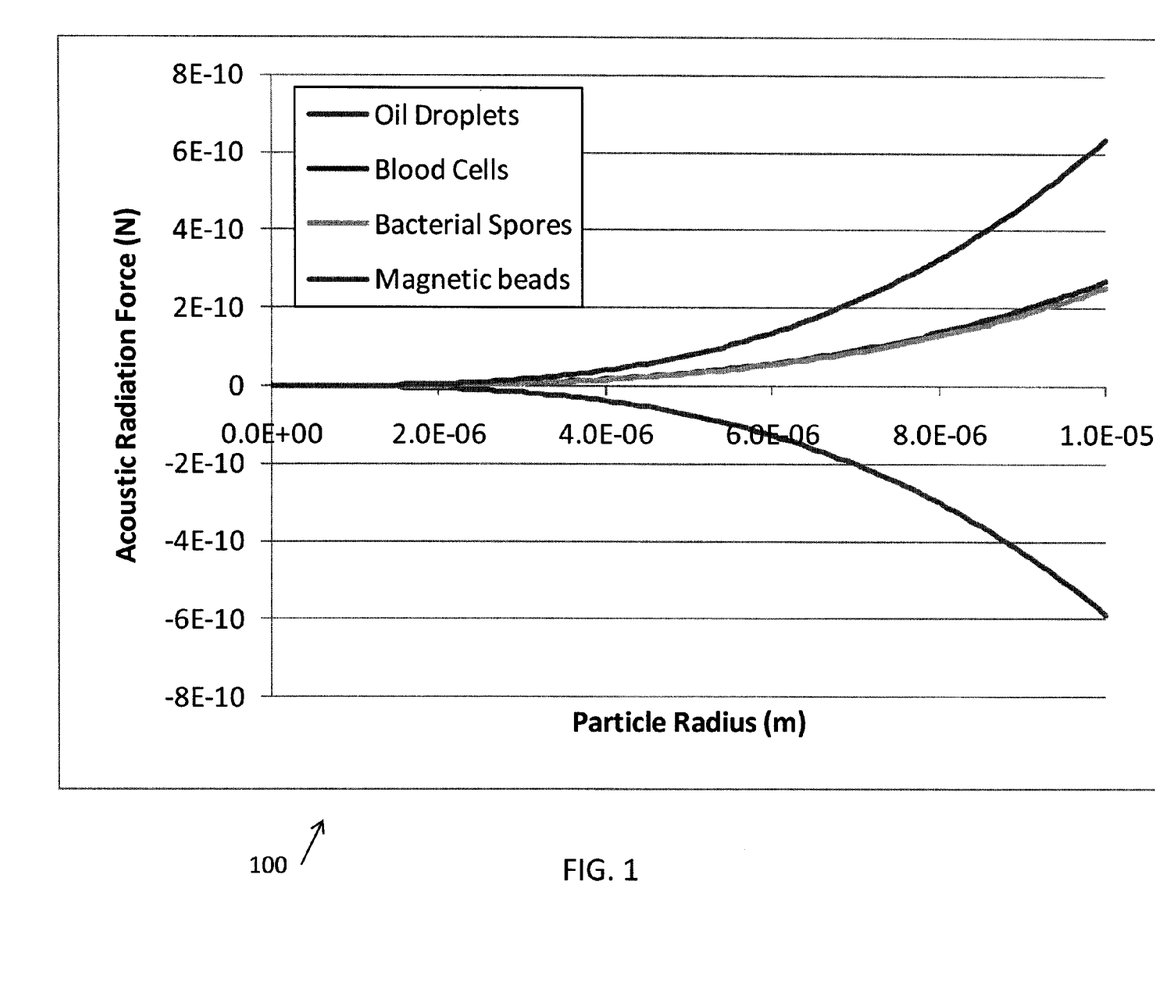
FIG. 1 is a diagram illustrating acoustic contrast, particle radius, and acoustic radiation force on particles for a given frequency of excitation and acoustic pressure level.

The current subject matter utilizes acoustophoresis, a low-power, no-pressure-drop, no-clog solid-state approach to particle removal from fluid dispersions: i.e., it is used to achieve separations that are more typically performed with porous filters and centrifuges, but it has none of the disadvantages of these systems. For example, the diagram 100 of FIG. 1 shows the forces for an applied acoustic frequency of 1 MHz (typical for an ultrasonic transducer) and an acoustic pressure of 0.5 MPa maximum at the antinodes (readily achieved in water). Achievement of higher applied acoustic frequencies and higher acoustic pressures will require better impedance matching. Examples of acoustic filters/collectors utilizing acoustophoresis can be found in commonly owned U.S. patent application Ser. Nos. 12/947,757, 61/261,686, 13/085, 299 and 61/342,307, the contents of all of these applications are hereby fully incorporated by reference. The acoustic radiation force ($F_{ac}$) acts on the secondary-phase particles (or fluid droplets), pushing them to the nodes (or antinodes) of the acoustic standing wave. The magnitude of the force depends on the particle density and compressibility relative to the fluid medium, and increases with the particle volume. The diagram 100 of FIG. 1 illustrates the acoustic force that operates on four different secondary phases in water as a function of the particle (or droplet) radius. The four secondary phases are hexanes (a mixture of hydrocarbons, a model for oils), red blood cells (a model for biological cells), bacterial spores (a model for "large" protein clusters and polystyrene beads such as are used for flow cytometry), and paramagnetic polystyrene beads (used for various biological capture and separation protocols). Parameters used in the calculation of the acoustic force are given below are in Table 1 (which are of particular interest regarding the algae parameters).

Figure 2:
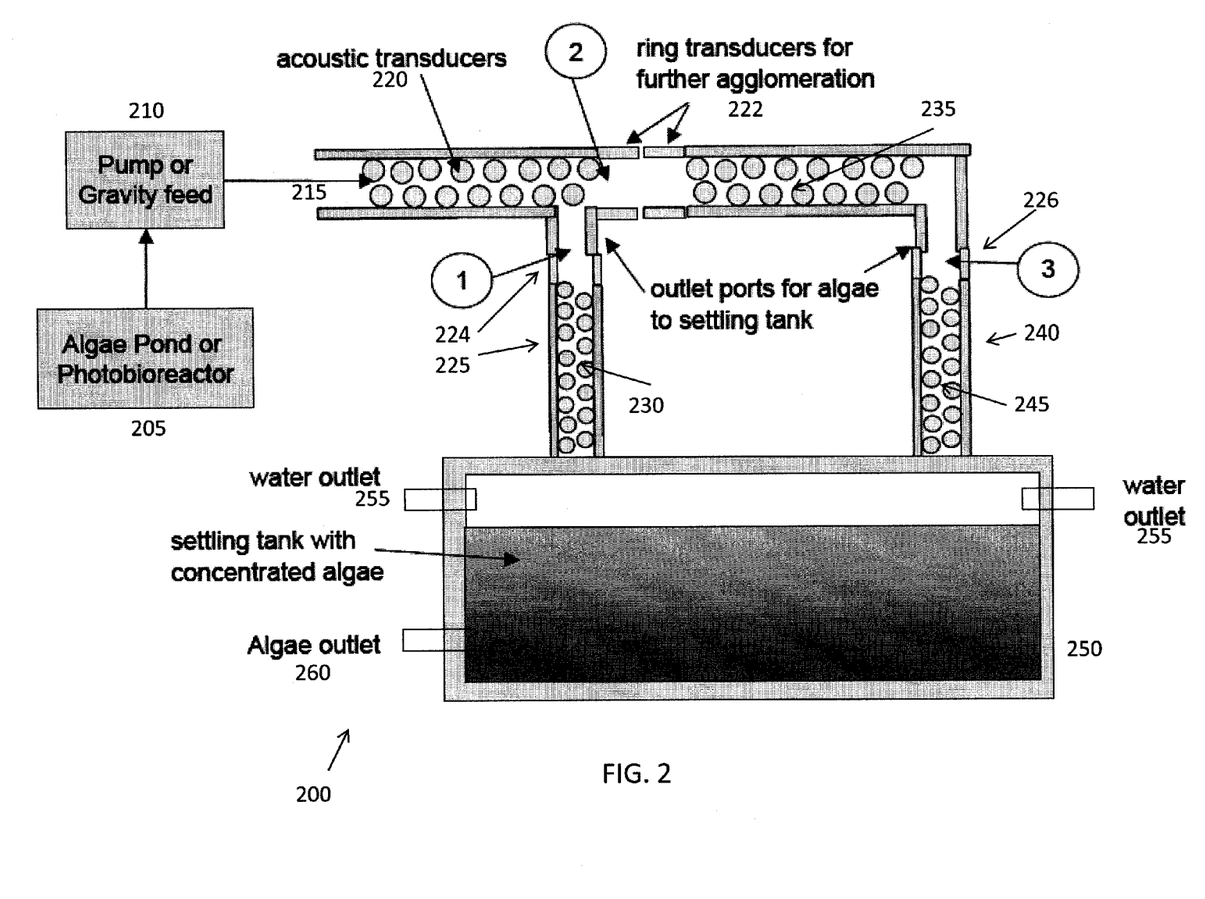
FIG. 2 is a diagram illustrating a first system for agglomeration of algae.

The current subject matter is advantageous in that it uses acoustophoresis for separations in extremely high volumes and in flowing systems with very high flow rates. Separations have been done for micron-size particles, for which the acoustophoretic force is quite small. For example, B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009; and B. Lipkens, J. Dionne, M. Costolo, A. Stevens, and E. Rietman, "Separation of bacterial spores from flowing water in macro-scale cavities by ultrasonic standing waves", (Arxiv) June 2010, the contents of both papers are hereby fully incorporated by reference) show that *Bacillus cereus* bacterial spores (a model for anthrax) have been trapped at 15% efficiency in an acoustophoretic cavity embedded in a flow system that can process drinking water at rates up to 120 mL/minute (1 cm/second linear flow). The concentration ratio has been as high as 1000 in a single-pass, small-scale prototype acousto-collector.

As stated above, the current subject matter is directed to agglomeration of microalgae for use in applications such as biofuel and nutraceutical production. The current techniques achieve low cost agglomeration by using the fact that ultrasonics will agglomerate and concentrate particles in the fluid in the acoustic standing wave. The ability to translate and concentrate these secondary phases is known as acoustophoresis (as will be further described below).

Physics of acoustophoresis. Acoustophoresis is the separation of a second phase (or phases) from a host fluid using sound pressure to create the driving force. An ultrasonic transducer operating at a fixed frequency f (Hz) is used to set up an acoustic standing wave in a fluid-filled cavity. The standing wave is characterized by a local pressure p that is a function of position (x) and time (t), $$p(x,t)=P\cos(kx)\sin(\omega t) \quad (1)$$

where P is the amplitude of the acoustic pressure; k is the wavenumber ($k=2\pi/\lambda$, where $\lambda$ is the wavelength), and $\omega=2\pi f$, where $\omega$ is the angular frequency. The pressure of the acoustic wave produces an acoustic radiation force $F_{ac}$ on secondary-phase elements according to $$F_{ac} = X\pi R_p^3 k\frac{P^2}{\rho_f c_f^2}\sin(2kx), \quad (2)$$

where $R_p$ is the particle radius, $\rho_f$ is the density of the fluid medium, $c_f$ is the speed of sound in the fluid, and X is the acoustic contrast factor, defined by $$X = \frac{1}{3}\left[\frac{5\Lambda-2}{1+2\Lambda} - \frac{1}{\sigma^2\Lambda}\right], \quad (3)$$

where $\Lambda$ is the ratio of the particle density to fluid density and $\sigma$ is the ratio of the speed of sound in the particle to the sound speed in the fluid. The acoustic radiation force acts in the direction of the acoustic field. The acoustic radiation force is proportional to the product of acoustic pressure and acoustic pressure gradient. An inspection of the acoustic radiation force shows that it is proportional to the particle volume, frequency (or wavenumber), the acoustic energy density (or the square of the acoustic pressure amplitude), and the acoustic contrast factor. Note also that the spatial dependency has twice the periodicity of the acoustic field. The acoustic radiation force is thus a function of two mechanical properties, namely density and compressibility.

TABLE 1

Properties of water and 4 selected secondary phases.

| Material | ρ (density) (kg/m³) | c (speed of sound) (m/s) | Λ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2.0 | 0.436 |

For three dimensional acoustic fields, a more general approach for calculating the acoustic radiation force is needed. Gor'kov's (1962) formulation can be used for this (see L. P. Gor'kov, "On the forces acting on a small particle in an acoustical field in an ideal fluid," Sov. Phys. Dokl., vol. 6, pp. 773-775, 1962). Gor'kov developed an expression for the acoustic radiation force $F_{ac}$ applicable to any sound field. The primary acoustic radiation force is defined as a function of a field potential U, given by $$F_{ac}=-\nabla(U), \quad (4)$$

where the field potential U is defined as $$U = V_0\left[\frac{\langle p^2(x,y,t)\rangle}{2\rho_f c_f^2}f_1 - \frac{3\rho_f\langle v^2(x,y,t)\rangle}{4}f_2\right], \quad (5)$$

and $f_1$ and $f_2$ are the monopole and dipole contributions defined by $$f_1 = 1 - \frac{1}{\Lambda\sigma^2}, \quad f_2 = \frac{2(\Lambda-1)}{2\Lambda+1}, \quad (6)$$

where p(x,y,z,t) is the acoustic pressure and v(x,y,z,t) is the fluid particle velocity. $V_o$ is the volume of the particle.

The diagram 100 of FIG. 1 shows the force required to capture small particles of various material properties. Each material has its own X parameter given in Equation [3]. In diagram 100, material properties (e.g. speed of sound, density) are used for the indicated material. The graph for bacteria spore is also valid for other materials of similar bulk modulus. Meaning smaller bacteria spore, very large protein clusters, and polystyrene microspheres would all be in this category. The blood cell curve is for any cells of similar bulk modulus. Finally the hexane curve would be valid for any tiny drops of oil-like material with the radius indicated on the curve. These curves are for, as an example, 1 MHz applied acoustic frequency and an acoustic pressure of 0.5 MPa. These are easily achieved control variables. Higher frequency and higher pressure require better impedance matching and will afford better separation of smaller particles—down to 10 s of nm.

FIG. 2 is a diagram 200 that illustrates a first system for algae agglomeration. Microalgae from a source 205 (such as an algae pond or photobioreactor, etc.) is pumped or gravity fed 210 along with its host fluid (e.g., water, etc.) into a primary flow channel 215 to generate a directional flow. Within the primary flow channel 215 are a first array of ultrasonic transducers 220 and a second array of ultrasonic transducers 235. These transducers 220 can be 1 cm, operate at 1 MHz, and have a flat profile. FIG. 6 is a diagram 600 illustrating a prototype of this portion of the system 200.

Extending from the primary flow channel 215 can be a first outlet channel 225 having a third array of transducers 230 interposed therein. The first outlet channel 225 can be positioned subsequent to the first array of transducers 220 in the flow direction. Extending from the primary flow channel 215 can be a second outlet channel 240 having a fourth array of transducer 245 interposed therein. The second outlet channel 255 can be positioned subsequent to the second array of transducers 235 in the flow direction. In some implementations, the primary flow channel 215 terminates at the second outlet channel 245. The host fluid after passing through the first array of transducers 220 can be diverted to the first outlet channel 225 or the second outlet channel 240 depending on the flow rate of the fluid (in relation to gravitational pull). In any event, the host fluid is passes by at least two arrays of transducers 220, 230 or 220, 235, 245 which act to agglomerate the algae.

Figure 3A:
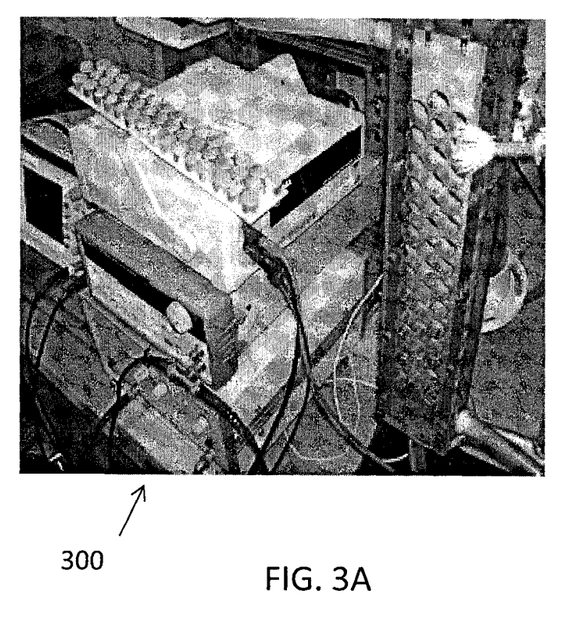
FIG. 3A is a photograph of experimental prototype.
Figure 3B:
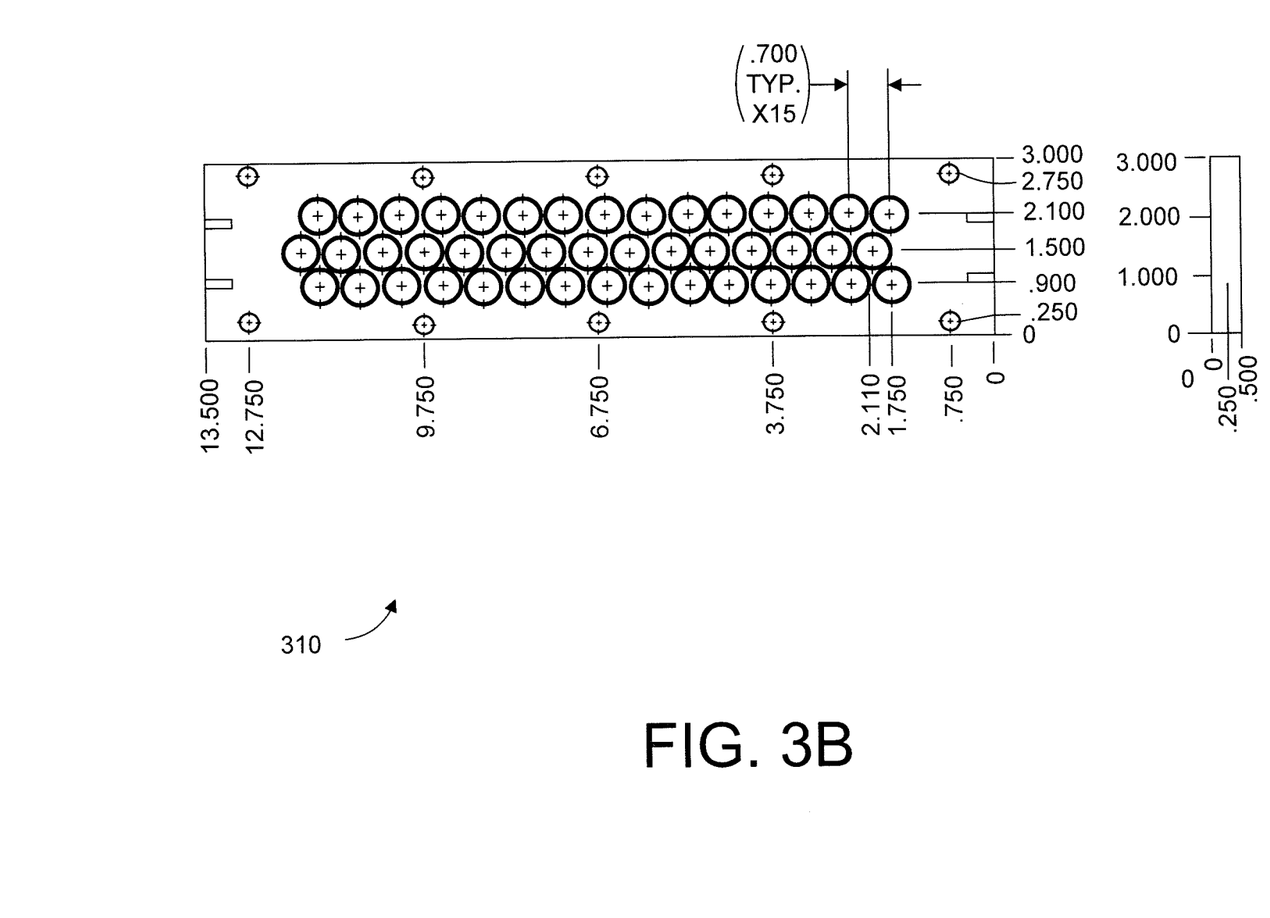
FIG. 3B is a diagram of array of small transducers

The arrays of transducers 220, 230, 235, 245 can comprise flat piezoelectric transducers. Each transducer has correspondingly positioned reflectors. The reflectors can be made of aluminum, steel, ceramic and the like. The flat transducers can be driven by an oscillating voltage in order to effect a resonance range of 100 kHz to 2 MHz (the voltage can be maximized in order to achieve maximum resonance without cavitation). In some implementations, the transducers are spaced in array with ½ inch spacing so as to affect a parallel array of parallel acoustic nodes. The array of transducers is shown in FIG. 3A-B (with a photograph 300 of an experimental prototype and a diagram 310 of an array of transducers).

To further aid agglomeration, ring transducers (sometimes referred to as cylindrical transducers) can be employed in each channel (primary flow channel 215 includes first ring transducers 222, first outlet channel 225 includes second ring transducers 224, and second outlet channel 240 includes third ring transducers 226). Each of the ring transducers can comprise one or more transducers at each position. In some implementations, the channels 220, 225, 240 can have a diameter of three inches so that the ring transducers 222, 224, 226 have similar diameters. The ring transducers can be driven by an oscillating voltage signal to effect a resonance range of 100 kHz to 2 MHz (the voltage can be maximized in order to achieve maximum resonance without cavitation). The ring transducers 222, 224, 226 can generate a concentric array of tube-shaped acoustic nodes of pressures in the range of 0.2 MPa to 200 MPa.

The first outlet channel 225 and the second outlet channel 240 both terminate in a settling tank in which water can be removed by one or more water outlets 255 and the resulting algae can be removed by one or more algae outlets 260. The algae outlet 260 can employ a variety of mechanisms (e.g., a screw/auger feeder, etc.) in order to facilitate transport of the highly agglomerated algae.

Figure 5:
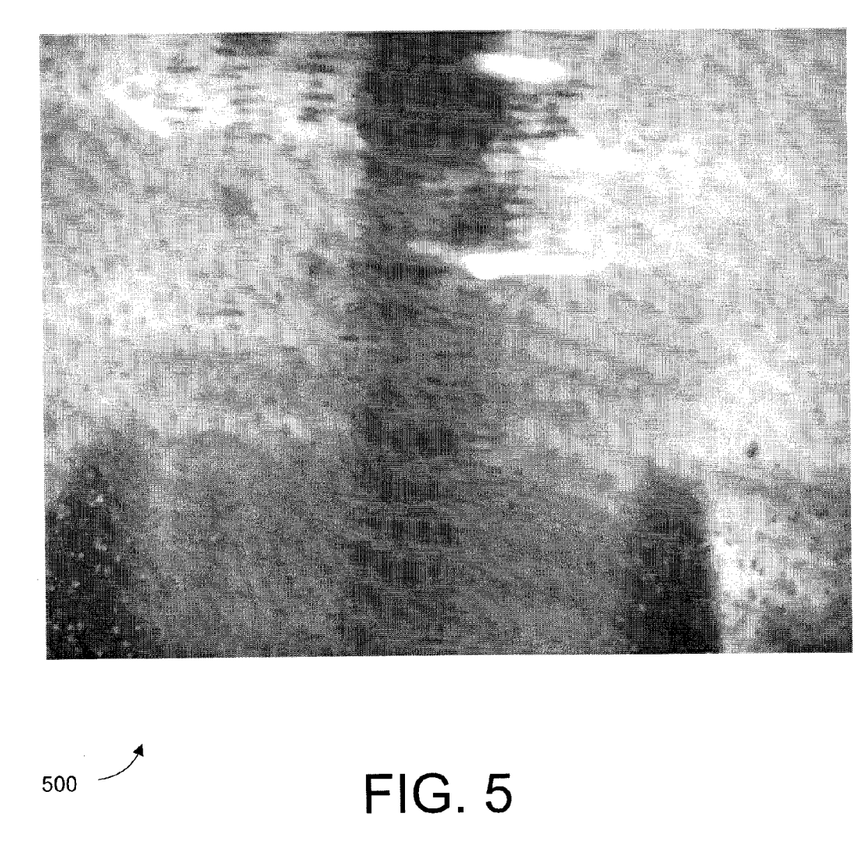
FIG. 5 is a photograph illustrating acoustic trapping of microalgae.

FIG. 5 is a diagram 500 showing the acoustophoretic collection of algae in a flowing water stream. A flat, circular transducer is used in the acoustocollector 600 of FIG. 6 (which can be of the sort described in co-pending U.S. patent application Ser. Nos. 13/085,299 and 61/342,307, the contents of both of which are hereby fully incorporated by reference). The pressure field of this transducer is a Bessel function that has a radial component in addition to the linear standing wave. The radial component acts to hold the captured algae in the column against the fluid flow. The trapped algae are then further concentrated in region by gravitational settling or by being driven to a collector pocket through a slow frequency sweeping (see, for example, Lipkens et al B. Lipkens, M. Costolo, and E. Rietman, "The effect of frequency sweeping and fluid flow on particle trajectories in ultrasonic standing waves", IEEE Sensors Journal, Vol. 8, No. 6, pp. 667-677, 2008; B. Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008; B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A) 2008, the contents of each are hereby fully incorporated by reference).

Figure 6A:
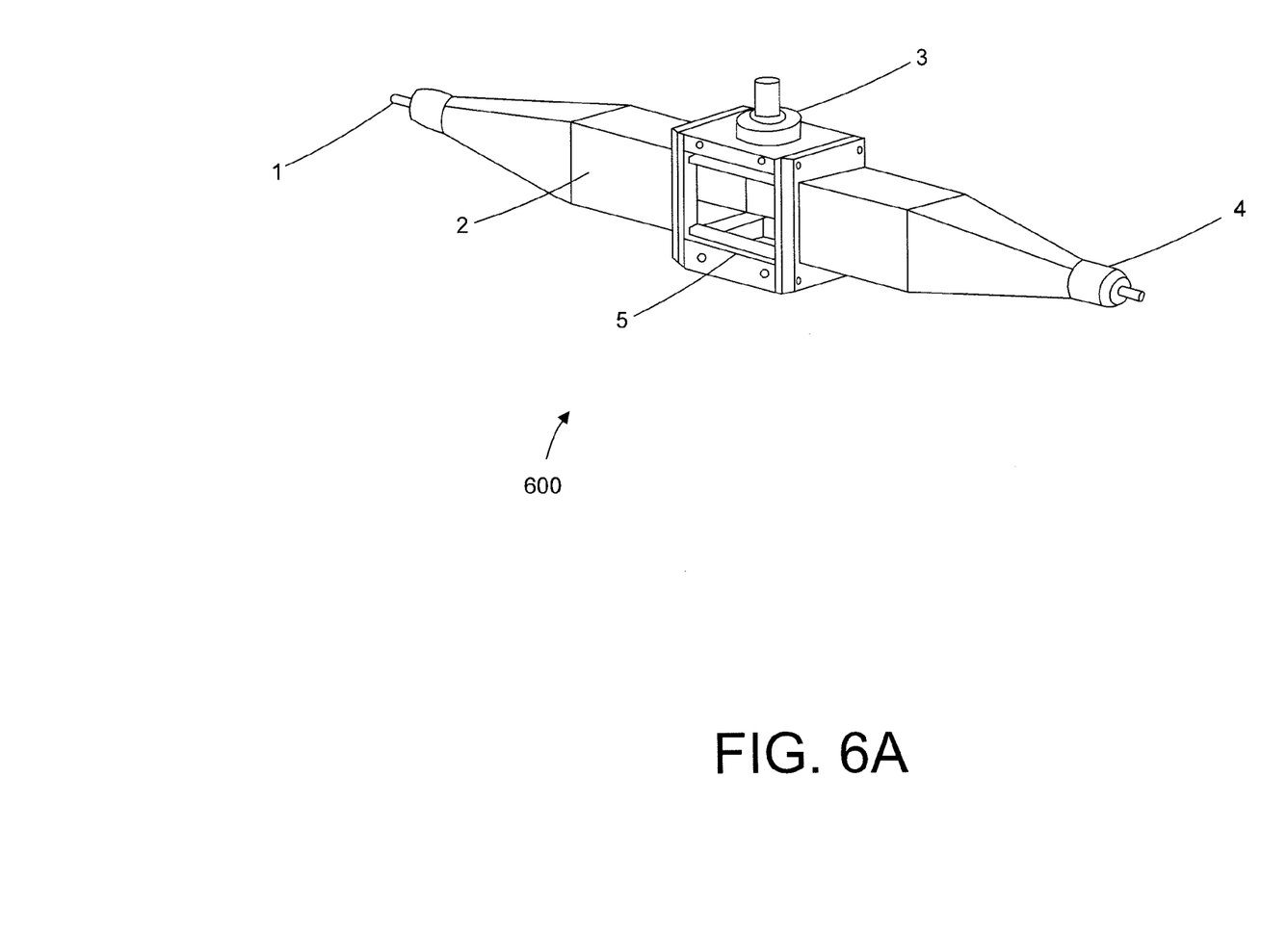
FIG. 6A is a diagram illustrating of a sample acoustocollector.
Figure 6B:
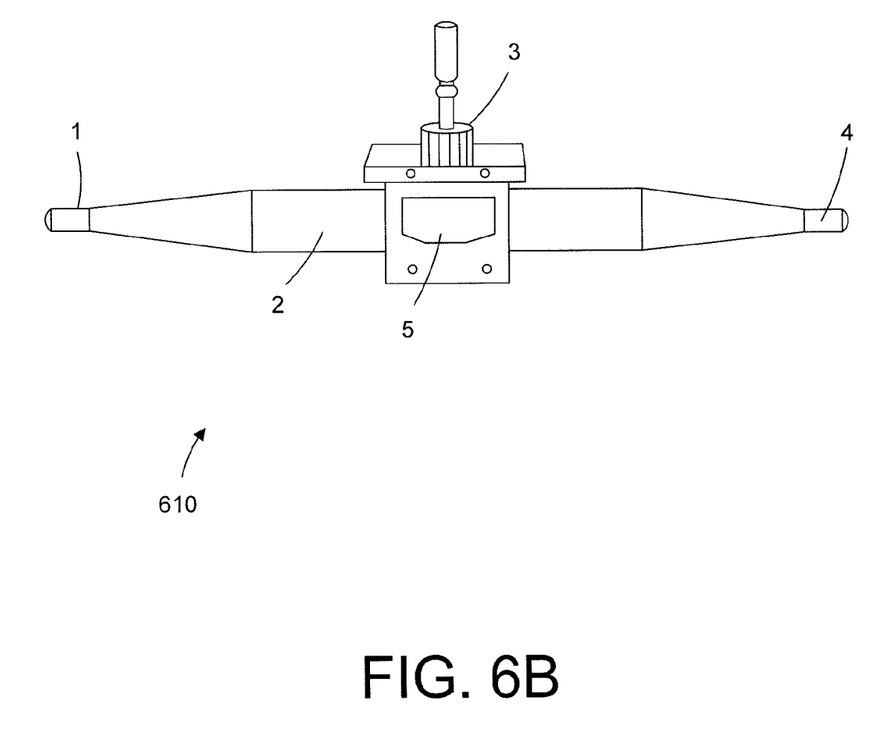
FIG. 6B is a photograph illustrating an experimental acoustocollector.

As an example using the acoustocollector 600 of FIG. 6, *Dunaliella Salina* were grown in a bottle filled with salt water and placed under a grow light. The algae were removed from the bottle through tubes that pass them into a flow channel and past the acoustic transducer. The flow chamber was horizontal with the transducer on top facing downward. Therefore, the acoustic standing wave is in the vertical direction. The transducer is a PZT-4 2 MHZ transducer. A peristaltic pump was used to generate fluid flow rates that were typically about 50 ml/min.

The acoustic transducer was connected to an amplifier which receives its signal from a function generator and operates at about 15 Vrms. Once the fluid flow and the acoustic transducer are turned on, trapping and concentration of microalgae takes place instantaneously. The microalgae are trapped in the acoustic field against the fluid drag force by means of the action of the acoustic radiation force. The collection of microalgae continues over time and eventually, typically after several minutes, large, beam-like collections of microalgae can be seen in the region between the transducer face and the opposition reflective wall. A typical result of the acoustic trapping of microalgae for about 15 to 20 minutes in the acoustocollector 500 of FIG. 5, as shown in the diagram 400 of FIG. 4. The results of this experiment clearly demonstrate the capabilities to use acoustophoresis to concentrate and separate the microalgae from water. The diagram 700 of FIG. 7 shows algae-based biofuel being separated from the emulsion of oil, cell extract, and algae agglomerates.

Figure 4:
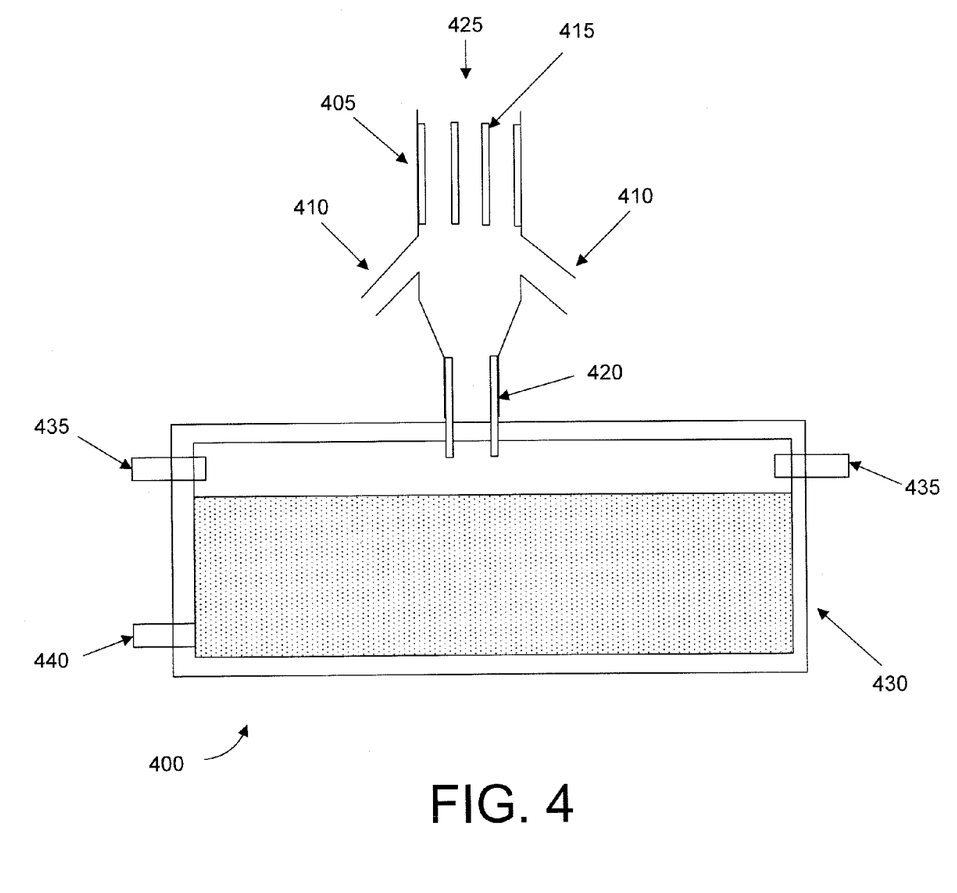
FIG. 4 is a diagram illustrating a second system for agglomeration of algae.

FIG. 4 is a diagram 400 that illustrates a second system for algae agglomeration. Algae in a host fluid are inserted into a flow chamber 405 that includes at least one algae-host fluid inlet 410 (which may be coupled to the flow chamber at an acute angle directed upwards). The flow chamber includes a first array of ring-shaped ultrasonic transducers 415 (e.g., transducers operating at 1 MHz, etc.) disposed in an upper portion of the flow chamber 405 above the algae-host fluid inlet(s) 410. The flow chamber 405 includes a second array of tube-shaped ultrasonic transducers 420 situated below the algae-host fluid inlet(s) 410. The flow chamber 405 includes a water outlet 425 on an upper portion. The flow chamber 405 terminates on a lower portion into a settling tank 430 (the lower portion can in some implementations be tapered). The host fluid and algae enters the first transducer array 415 and is subjected to high acoustic force, which agglomerates the algae and traps them as the water flows through the first array of transducers 415. As the mass of algae become critical, the algae clumps drop down into the collection tank 430 from gravitational settling and water exits out the water outlet 425 top (e.g., for recycling to a bioreactor, algae pond or for further processing such as chromatography, etc.). The algae and host-fluid is subject to the second array of transducers 420 prior while flowing to the settling tank 430 to further aid agglomeration of the algae. The settling tank 430 can include at least one water outlet 435 to allow for the removal of water as well as an algae outlet 440 to allow for the collection/removal/transport of the algae. Again, a removal mechanism, such as screw or auger, can be used to transport the agglomerated algae from the tank and the water is removed from the top as overflow. The overflow water can be recycled for use in the algae bioreactors or algae growth pond.

Figure 7A:
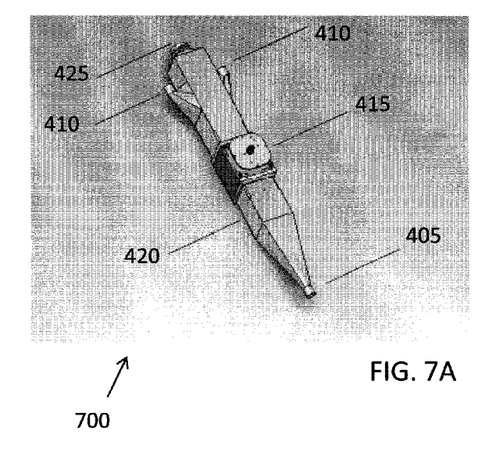
FIG. 7A is a diagram illustrating a sample flow chamber.
Figure 7B:
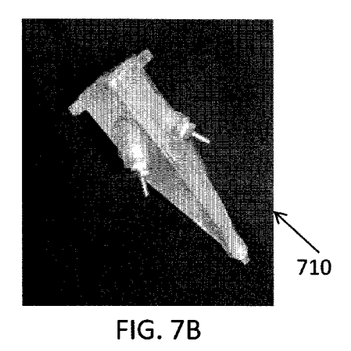
FIG. 7B is a photograph illustrating an experimental flow chamber.
Figure 8:
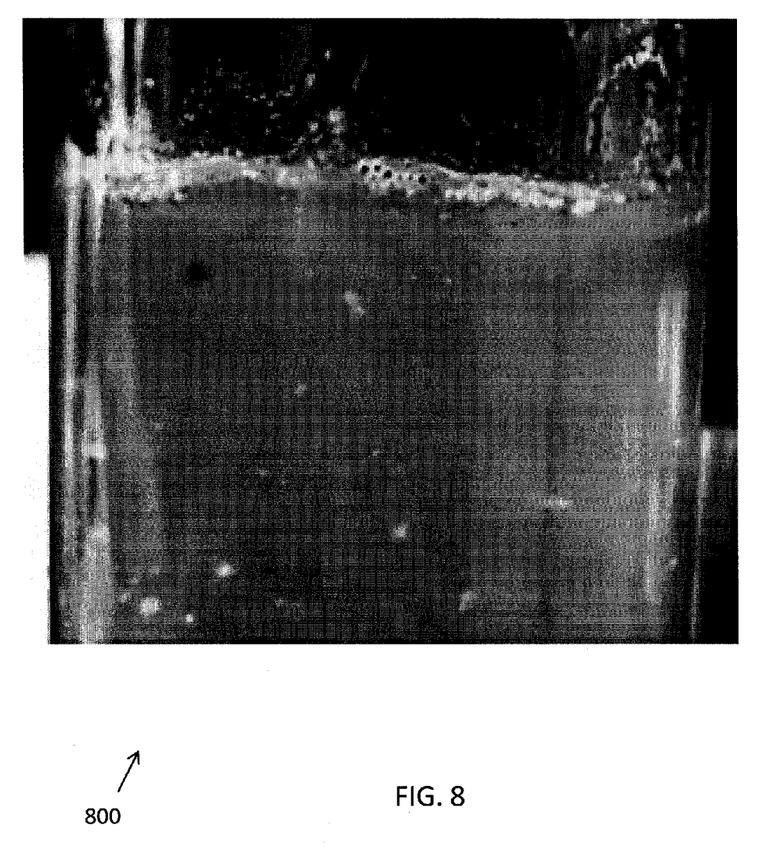
FIG. 8 is a photograph illustrating algae-based biofuel being separated from an emulsion of oil, cell extract, and algae agglomerates.
Figure 9:
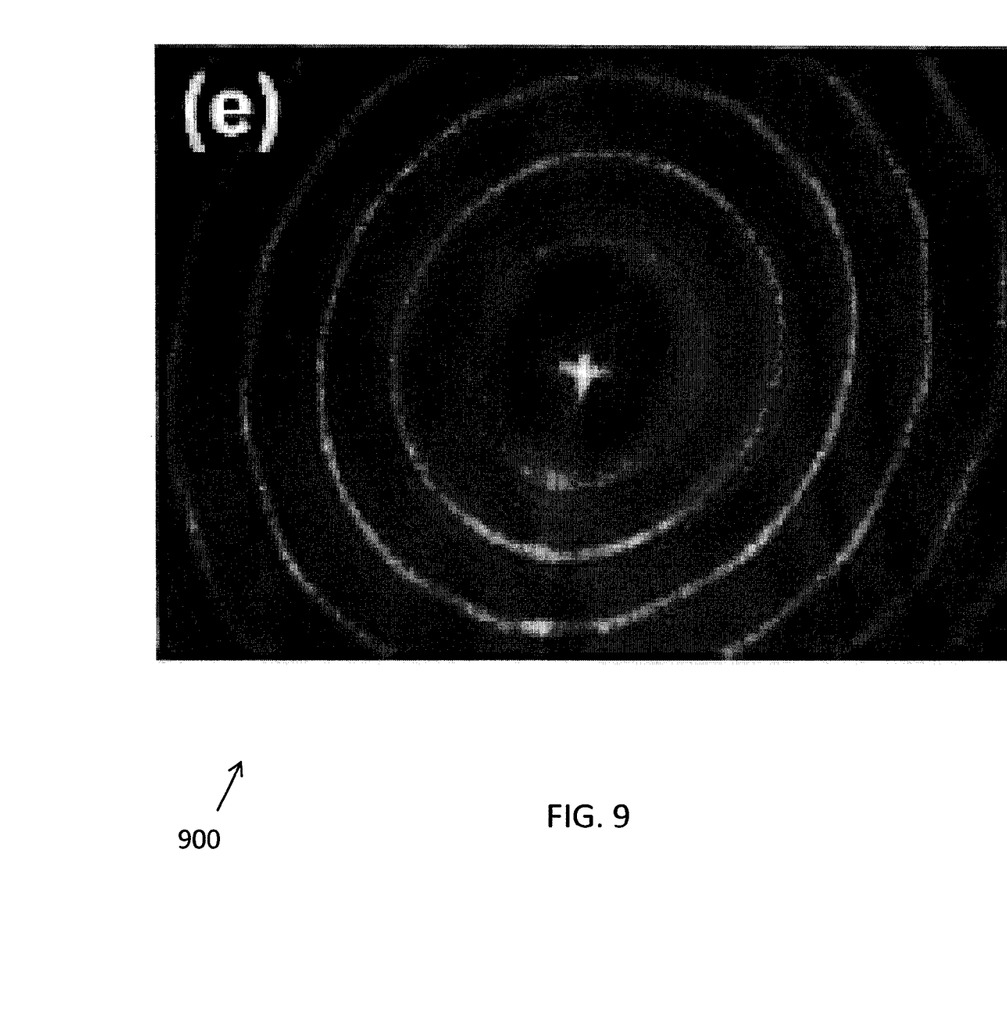
FIG. 9 is a photograph illustrating acoustic standing waves in a ring-shaped transducer.

FIG. 7 is a diagram 700 showing one example of a flow chamber 405. Water (or other host-fluid) enters the angled inlet ports 410. The algae-water enters the ring-shaped transducers 415 with ring-shaped standing waves inside. These standing waves can have very high pressure on the order of 100 MPa. In related experiments, the inventors sealed a ring or tube-shaped transducer with glycerin and powered it up to 412 kHz at 100 V(pp). The inventors then measured optically the deflection of a laser beam due to pressure modulations in the fluid. The pressures calculated, based on refractive index, were as high as 100 MPa. It was observed that these pressures were so extreme that they can agglomerate nanoparticles of metal oxide. Diagram 900 of FIG. 9 shows the acoustic standing waves in a tube-shaped transducer.

While this specification contains many specifics, these should not be construed as limitations on the scope of what is claimed or of what may be claimed, but rather as descriptions of features specific to particular variations. Certain features that are described in this specification in the context of separate variations can also be implemented in combination in a single variation. Conversely, various features that are described in the context of a single variation can also be implemented in multiple variations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A system comprising:
a primary flow channel through which is flowed a mixture of a host fluid and microorganisms, the primary flow channel having an inlet and extending to a terminus;
a first outlet channel extending from the primary flow channel to a settling tank, said first outlet channel beginning at a point between the inlet and the terminus;
a second outlet channel extending from the terminus of the primary flow channel at the terminus to the settling tank, wherein the primary flow channel terminates at the second outlet channel;
a first array of transducers disposed within the primary flow channel between the inlet and the first outlet channel for acoustically agglomerating the microorganisms; and
a second array of transducers disposed within the primary flow channel between the first outlet channel and the terminus for further acoustically agglomerating the microorganisms;
a third array of transducers disposed within the first outlet channel for further acoustically agglomerating the algae;
wherein the settling tank collects the host fluid and the microorganisms after agglomeration by at least one of the first and second arrays of transducers, the settling tank including at least one host fluid outlet through which the host fluid is removed after the microorganisms has settled and at least one microorganisms outlet to facilitate removal of the microorganisms.

2. A system as in claim 1, wherein the host fluid and microorganisms are gravitationally fed into at least one of the primary flow channel, the first outlet channel and the second outlet channel.

3. A system as in claim 1, further comprising a pump for introducing the host fluid and microorganisms into the primary flow channel.

4. A system as in claim 1, wherein the host fluid is water.

5. A system as in claim 1, further comprising a reservoir containing the host fluid and microorganisms prior to introduction in to the primary flow channel.

6. A system as in claim 1, wherein the transducers are flat transducers.

7. A system comprising:
a primary flow channel through which is flowed a mixture of a host fluid and microorganisms, the primary flow channel having an inlet and extending to a terminus;
a first outlet channel extending from the primary flow channel at a point between the inlet and the terminus to a settling tank;
a second outlet channel extending from the primary flow channel at the terminus to the settling tank;
a first array of transducers disposed within the primary flow channel between the inlet and the first outlet channel for acoustically agglomerating the microorganisms;
a second array of transducers disposed within the primary flow channel between the first outlet channel and the terminus for further acoustically agglomerating the microorganisms;
a third array of transducers disposed within the first outlet channel for further acoustically agglomerating the microorganisms; and
a fourth array of transducers disposed within the second outlet channel for further acoustically agglomerating the microorganisms.

8. A system as in claim 7, further comprising:
at least one first ring transducer disposed within the primary flow channel between the first array of transducers and the second array of transducers for further acoustically agglomerating the microorganisms;
at least one second ring transducer disposed within the first outlet channel between the primary flow channel and the third array of transducers for further acoustically agglomerating the microorganisms; and
at least one third ring transducer disposed within the second outlet channel between the primary flow channel and the fourth array of transducers for further acoustically agglomerating the microorganisms.

9. A system comprising:
a flow chamber through which is flowed a mixture of a host fluid and microorganisms, the flow chamber comprising:
at least one inlet through which the host fluid and microorganisms enters the flow chamber and is directed upwards;
at least one water outlet at an upper portion of the flow chamber through which water exits the flow chamber;
an microorganisms outlet at a lower portion of the flow chamber through which agglomerated microorganisms exits the flow chamber into a settling tank; and
a first array of transducers disposed between the at least one inlet and the at least one water outlet for acoustically agglomerating the microorganisms; and a second array of transducers disposed between the microorganisms outlet of the flow chamber and the settling tank for further acoustically agglomerating the microorganisms;

wherein the settling tank is located below the flow chamber, and includes a host fluid outlet for removal of the host fluid and an microorganisms outlet for removal of the microorganisms.

10. A system as in claim 9, further comprising a pump for introducing the host fluid and microorganisms into the flow chamber.

11. A system as in claim 9, wherein the host fluid is water.

12. A system as in claim 9, further comprising a reservoir containing the host fluid and microorganisms prior to introduction in to the flow chamber.

13. A system as in claim 9, wherein the transducers are tubular transducers.

14. A system as in claim 13, wherein the tubular transducers are positioned in parallel in a vertical orientation.

* * * * *